(12) United States Patent
Dibie

(10) Patent No.: US 6,183,509 B1
(45) Date of Patent: Feb. 6, 2001

(54) ENDOPROSTHESIS FOR THE TREATMENT OF BLOOD-VESSEL BIFURCATION STENOSIS AND PURPOSE-BUILT INSTALLATION DEVICE

(76) Inventor: Alain Dibie, 37 avenue de Lowendale, 75015 Paris (FR)

(*) Notice: Under 35 U.S.C. 154(b), the term of this patent shall be extended for 0 days.

(21) Appl. No.: 08/945,973
(22) PCT Filed: May 3, 1996
(86) PCT No.: PCT/IB96/00403
  § 371 Date: Jan. 26, 1998
  § 102(e) Date: Jan. 26, 1998
(87) PCT Pub. No.: WO96/34580
  PCT Pub. Date: Nov. 7, 1996

(30) Foreign Application Priority Data

May 4, 1995 (FR) .................................................. 9505334

(51) Int. Cl.[7] .............................................................. A61F 2/00
(52) U.S. Cl. ............................ 623/1.35; 623/1.37; 623/1.16
(58) Field of Search .................................. 623/1.15, 1.16, 623/1.37, 1.35, 23.7, 1.42

(56) References Cited

U.S. PATENT DOCUMENTS

| | | | |
|---|---|---|---|
| 4,994,071 | 2/1991 | MacGregor | 606/194 |
| 5,195,984 | 3/1993 | Schatz | 606/195 |
| 5,342,387 | * 8/1994 | Summers | 623/12 X |
| 5,723,004 | * 3/1998 | Dereume et al. | 623/1.35 |
| 5,755,771 | * 5/1998 | Penn et al. | 623/1.15 |
| 5,782,906 | * 7/1998 | Marshall et al. | 623/1.15 |
| 5,893,887 | * 4/1999 | Jayaraman | 623/1.37 X |

FOREIGN PATENT DOCUMENTS

| | | | |
|---|---|---|---|
| 90 14 845 | 10/1990 | (DE) | A61M/25/10 |
| 0 551 179 | 1/1993 | (EP) | A61F/2/06 |
| 0 646 365 | 9/1994 | (EP) | A61F/2/06 |
| 2 678 508 | 7/1991 | (FR) | A61F/2/06 |
| WO 95/08965 | 9/1994 | (WO) | A61F/2/04 |

* cited by examiner

Primary Examiner—Michael J. Milano
Assistant Examiner—Brian E. Pellegrino
(74) Attorney, Agent, or Firm—Blakely Sokoloff Taylor & Zafman

(57) ABSTRACT

An endoprosthesis for the treatment of blood-vessel bifurcation stenosis. The endoprosthesis comprises three tubular sections (110, 120 and 140) and two connectors (130 and 150). A distal section (120) is aligned at least approximately with a proximal section (110). The first distal section is intended for insertion into a first blood vessel (T2) branching off on the bifurcation. The first distal section (120) is linked to the proximal section (110) by a first lateral connector (130). A second distal section (140), located at the side of the first distal section (120) is intended for insertion into a second vessel (T3) branching off from the bifurcation. The two distal sections (120 and 140) have their proximal ends linked by a second connector (150).

30 Claims, 4 Drawing Sheets

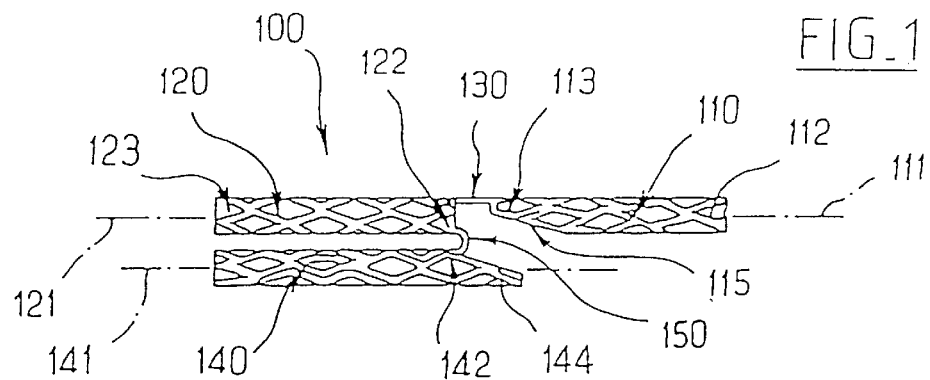
FIG_1
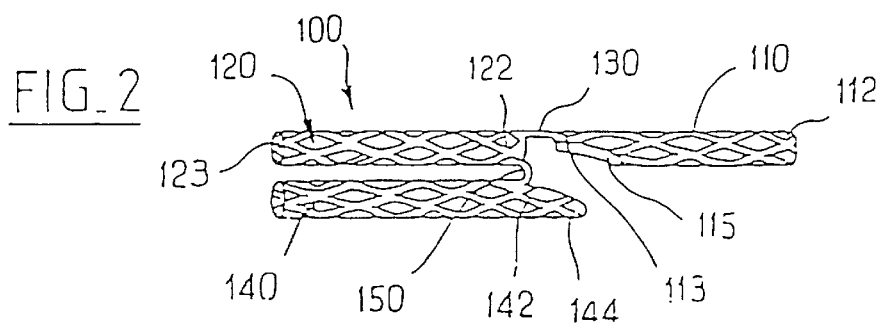
FIG_2
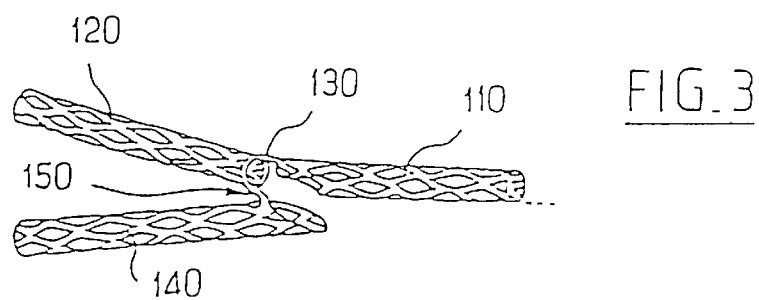
FIG_3
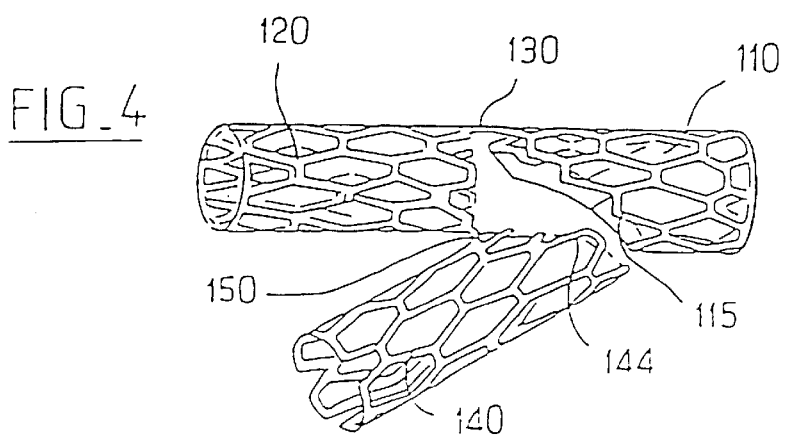
FIG_4

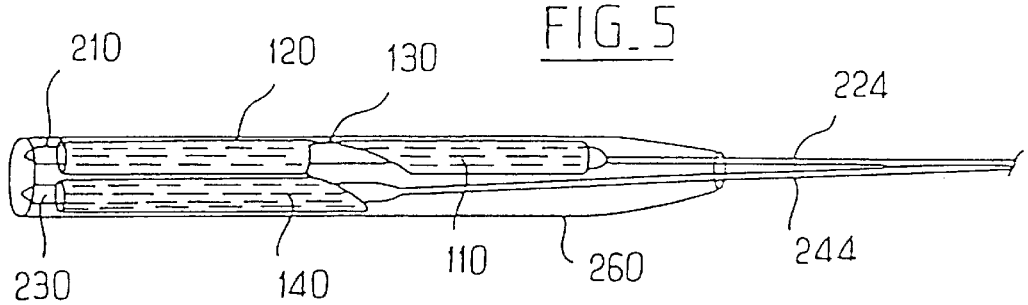
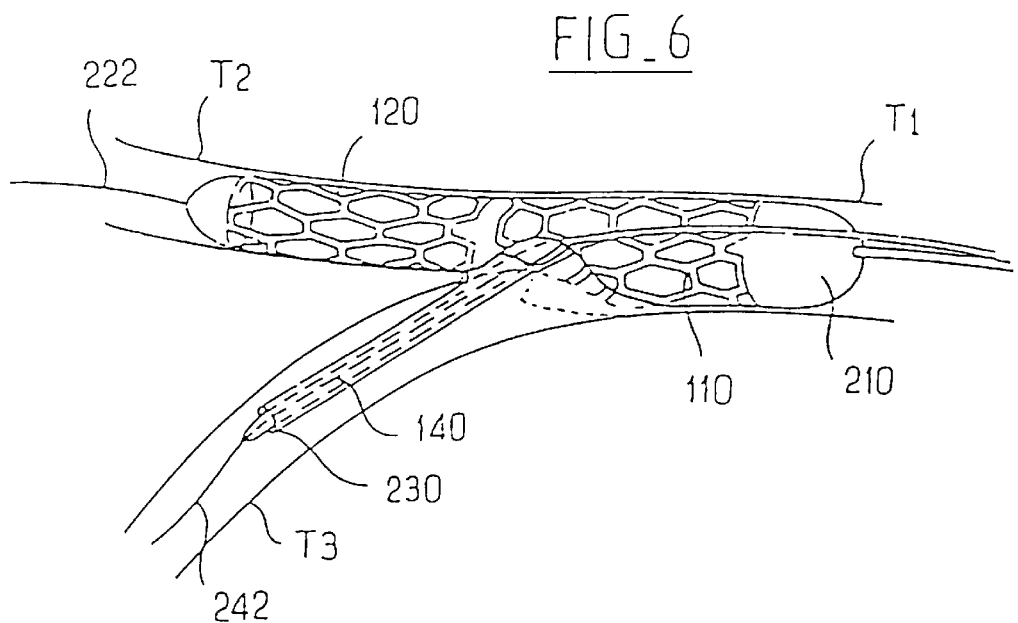
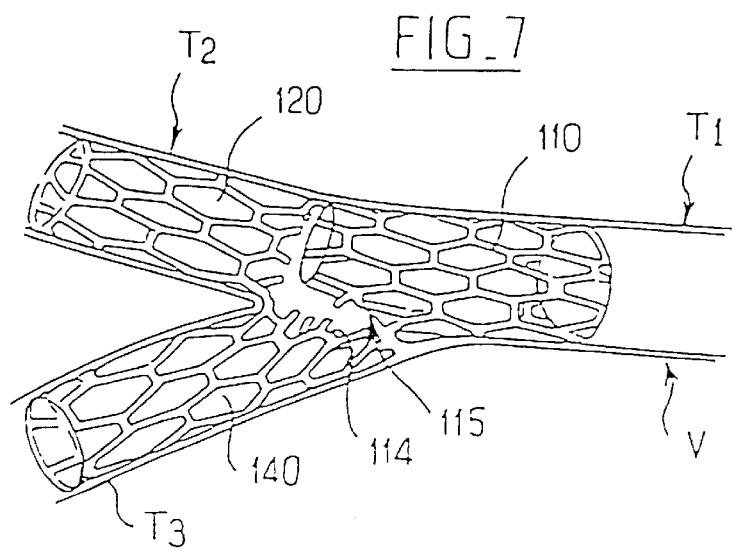

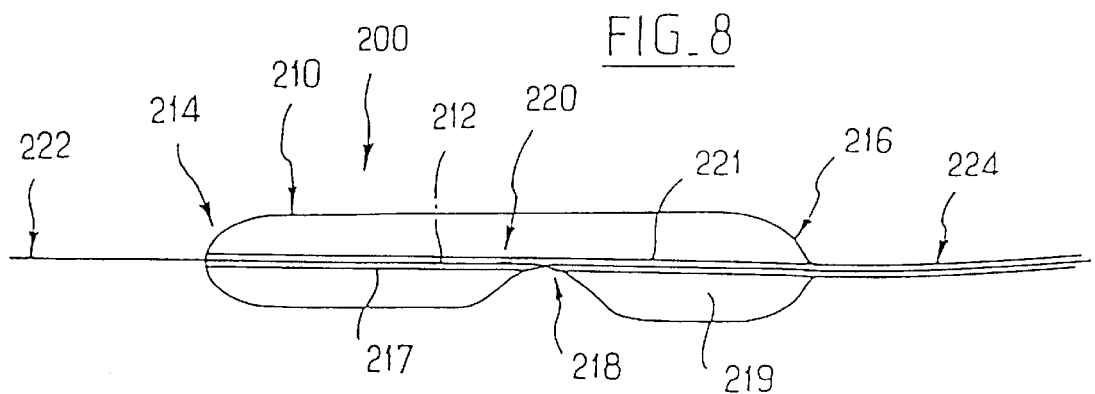
FIG_8
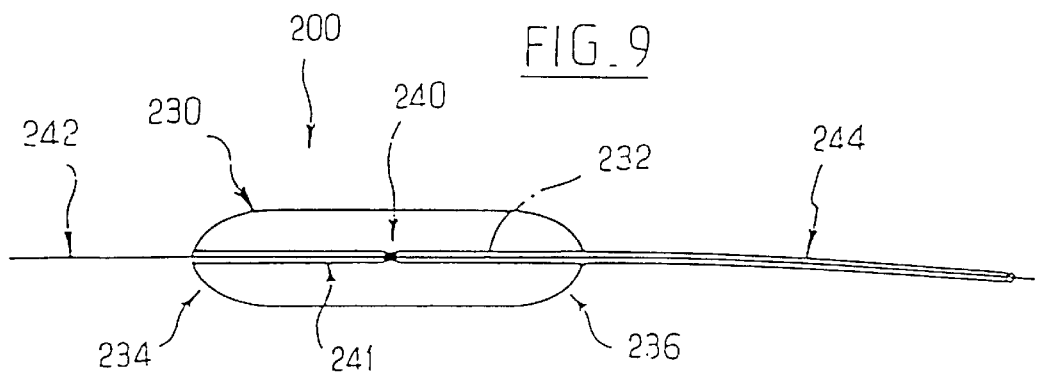
FIG_9
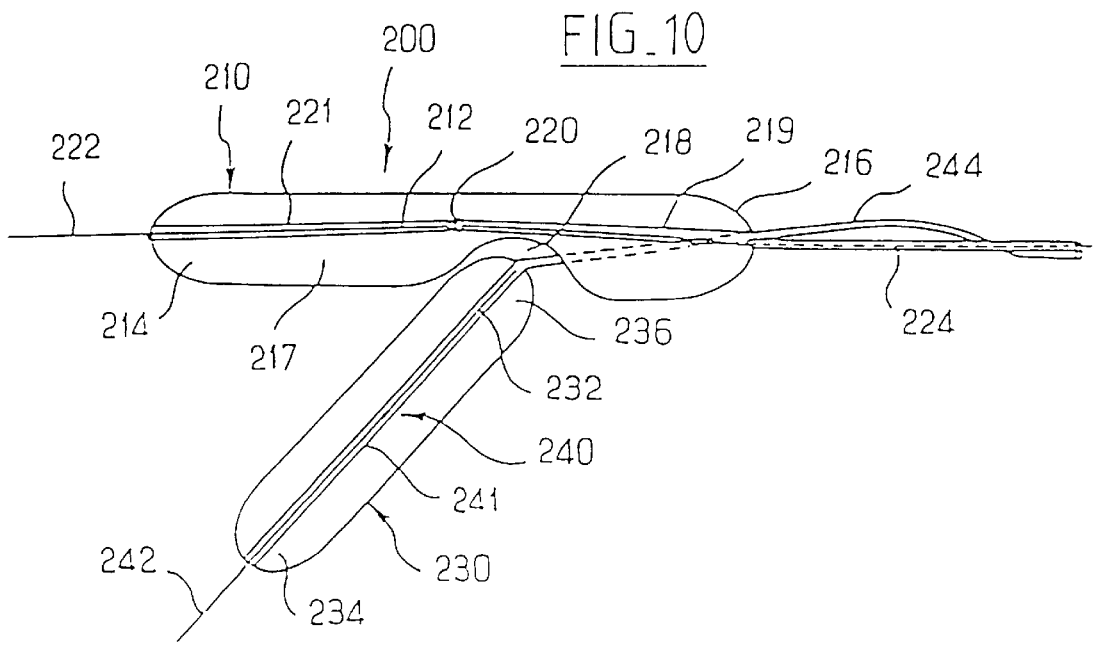
FIG_10

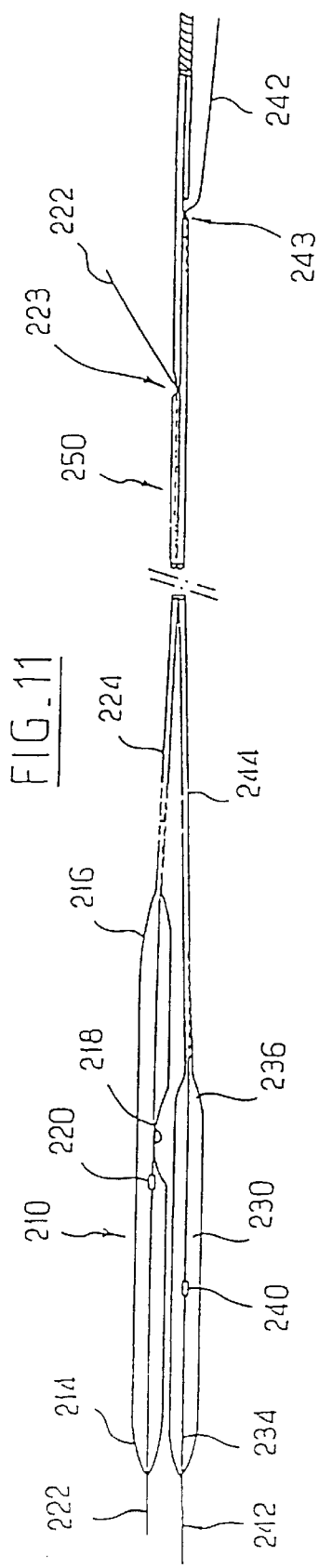
FIG._11
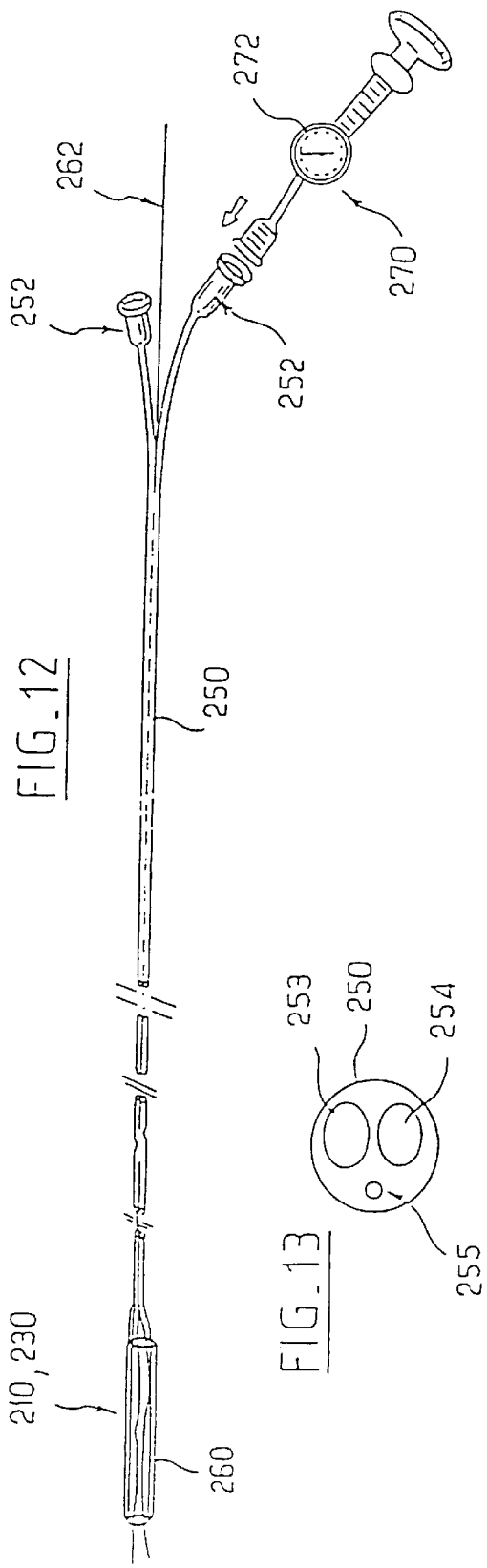
FIG._12
FIG._13

ENDOPROSTHESIS FOR THE TREATMENT OF BLOOD-VESSEL BIFURCATION STENOSIS AND PURPOSE-BUILT INSTALLATION DEVICE

FIELD

This invention relates to the field of endoprostheses for the treatment of blood-vessel bifurcation stenosis. In particular, this invention also relates to a purpose-built installation device.

BACKGROUND

It has already been suggested that stenosis found in coronary arteries be treated using endoprostheses formed from tubular structures perforated with a grid pattern of slits and consequently expandable following placement at the site of stenosis. In most cases these endoprostheses are expanded by inflating a balloon which is placed inside them and subsequently withdrawn.

Generally speaking, endoprostheses of this type may be said to have already given good service.

They are not, however, fully satisfactory.

The applicant has, in particular, observed that standard endoprostheses are not fully satisfactory when, as is frequently the case, there is stenosis at a blood-vessel bifurcation. In such cases, treatment using standard endoprostheses requires two separate endoprostheses. One of these is placed in each of the two vessels branching off from the bifurcation and their positioning in relation to each other is adjusted as finely as possible to ensure optimal cover of the bifurcation area.

SUMMARY

A primary goal of this invention is to develop existing endoprostheses in order to facilitate and improve treatment of blood-vessel bifurcation stenosis.

This goal is attained by this invention through the use of an endoprosthesis comprising three tubular sections and two connectors, namely:

a proximal section;

a first distal section aligned at least approximately with the proximal section and intended for insertion into one of the vessels branching off from the bifurcation, this distal section being attached to the proximal section by means of a laterally positioned connector; and a second distal section placed at the side of the first distal section and intended for insertion into the second vessel branching off from the bifurcation, the two distal sections having their proximal ends joined by the second connector.

In accordance with another advantageous feature of this invention, the distal end of the proximal section is chamfered and the proximal end of the second distal section is tapered at the other side of the second connector and fits into the chamfer in the proximal section.

The above-mentioned chamfered shapes and tapered ends may have a variety of embodiments. They may, in particular, be delimited by flat or curved surfaces.

Another important goal of this invention is to perfect the method of installing the above-mentioned endoprostheses.

According to this invention this goal is attained by using a double-balloon system, as follows:

a first balloon of suitable length for insertion into two approximately aligned sections of the blood vessel to be treated: the main stem and the first branching blood vessel, on either side of the bifurcation area respectively; and a second balloon of suitable nature for insertion into the second blood vessel branching off from the bifurcation.

In accordance with another advantageous feature of the invention, the first balloon incorporates a lateral recess to be positioned facing the bifurcation area with a view to housing the proximal end of the second balloon.

In accordance with another advantageous feature of this invention, the distal portion of the first balloon located downstream of the recess is of smaller diameter than the proximal portion of the balloon located upstream of the recess.

DRAWINGS

Further features, goals and advantages of the invention will be apparent on reading the following detailed description as illustrated in the corresponding accompanying drawings, which are given as non-exhaustive examples and in which:

FIG. 1 is a schematic side view of an endoprosthesis in accordance with this invention;

FIG. 2 is a perspective view of the same endoprosthesis;

FIG. 3 is another perspective view of the same endoprosthesis after relative inclination of the distal sections;

FIG. 4 is a view of the same endoprosthesis following expansion of the various tubular sections from which it is formed;

FIG. 5 is a schematic illustration of an endoprosthesis combined with the device for installing it, prior to implantation in a stenosis-affected bifurcation area;

FIG. 6 is a view of the same instrument following implantation in a bifurcation and expansion of the proximal section and one distal section;

FIG. 7 is a view of the same endoprosthesis after expansion of the three sections from which it is formed;

FIG. 8 is a schematic side view of the first balloon in accordance with the invention;

FIG. 9 is a side view of the second balloon in accordance with the invention;

FIG. 10 is an overall view of an installation instrument comprising two balloons working together in accordance with the invention;

FIG. 11 is another side view of the balloon-based installation system in accordance with the invention;

FIG. 12 is an overall view of the same balloon-based installation tool combined with means of inflation; and FIG. 13 is a schematic cross-sectional view of a feeder tube for the double-balloon system.

DETAILED DESCRIPTION

The first item described will be the structure of endoprosthesis 100 in accordance with the invention and illustrated in FIGS. 1 to 7. As was mentioned earlier, endoprosthesis 100 comprises three tubular sections (110, 120 and 140) and two connectors (130 and 150).

The first section (110) is a proximal section having as its centre axis 111. It is intended for insertion into main stem T1 of blood vessel V for treatment, upstream of the bifurcation.

The first distal section (120) having as its section axis 121 is at least approximately aligned with proximal section 110 prior to use. This first distal section 120 is intended for insertion into blood vessel T2 branching off from the bifurcation as is seen in particular in FIGS. 6 and 7.

The first distal section (120) is attached to proximal section 110 by the first lateral connector (130).

The second distal section (140), having as its axis 141, is positioned at the side of the first distal section (120), and has the advantage of being parallel to the latter, prior to use. The second distal section (140) is intended to be inserted into blood vessel T3 branching off from the bifurcation, as is seen in particular in FIGS. 6 and 7.

The two distal sections 120 and 140 have their proximal ends (122 and 142) linked by the second connector (150).

Each of section 110, 120 and 140 is preferably formed from a tubular component perforated with a grid pattern of slits such that the structure of sections 110, 120 and 140 allows them to expand along their circumferences.

In practice, section 110, 120 and 140 of endoprosthesis 100 can be manufactured from extruded cylindrical parts made of a bendable metal alloy such as 316L stainless steel. The external diameter of section of 110, 120 and 140 typically ranges from 1 to 1.2 mm prior to use.

There can be a range of variants of the grid pattern cut into sections 110, 120 and 140. The opening may take the form of a hexagon or diamond, as shown in the accompanying figures, taking on the appearance of grating following expansion against the inner surface of the coronary artery by means of a cylindrical balloon placed inside.

As the basic structure of expandable tubular components 110, 120 and 140 and the material from which they are made are familiar to those skilled in the art, these particulars will not be described in detail in what follows.

The three sections 110, 120 and 140 are preferably of equal diameter prior to expansion, i.e. prior to use.

The respective axes (111, 121 and 141) of sections 110, 120 and 140 are coplanar and determine a plane of symmetry for the endoprosthesis. This plane of symmetry is parallel to the plane of FIG. 1.

The first connector (130) has as its centre the above-mentioned plane of symmetry determined by axes 111, 121 and 141.

Connector 130 links an area of distal end 113 of proximal section 110 with an area of proximal end 122 of the first distal section (120). Yet more specifically, articulation 130 preferably consists of a strip of constant width parallel to axes 111 and 121. Articulation 130 is diametrically opposite the second distal section (140) with respect to axes 111 and 121.

Distal end 113 of proximal section 110 is provided with chamfer 115 in its peripheral area situated opposite connector 130. Chamfer 115 can be determined by a plane that is inclined with respect to axis 111, perpendicular to the above-mentioned plane of symmetry or, again, be curved, for instance, concave with respect to distal section 120. Angular opening of the wall of proximal section 110 thus increases starting from connector 130 and turns through 360°, i.e. a complete tubular form around axis 111.

This cant (115) forms a type of arch located on the side opposite connector 130 embodying in the cylindrical structure forming proximal section 110 the shape of the ostium of the blood vessel branching off from the coronary bifurcation onto which it will be applied.

Furthermore, proximal end 142 of the second distal section (140) is tapered at the other side of the second connector (150). It stretches forwards in its peripheral area opposite the second connector (150). This tapered portion (144) may also be determined by a plane that is inclined with reference to axis 121, perpendicular to the plane of symmetry or, again, by a curved surface.

After expansion, as is illustrated in FIG. 4 for example, when the endoprosthesis is installed at the bifurcation of the two coronary arteries, distal portion 113 with the corner cut off (115) of proximal section 110 is fixed together harmoniously with the proximal (144) of section 140 of the endoprosthesis and ensures maximum coverage of the dilated coronary bifurcation area.

In this way, once in place, the whole of the grid of the bifurcated endoprosthesis (100) covers the proximal and distal portions of the two coronary branching arteries and the whole of the dilated bifurcation area.

The first connector (130) preferably forms an integral part, i.e. it is not joined onto sections 110 and 120.

In other words, the first connector (130) and sections 110 and 120 are preferably manufactured from a single part in which connector 130 is formed via machining.

The second connector (150) is also centred with reference to the plane of symmetry determined by axes 111, 121 and 141.

However, whereas the first connector (130) extends in a direction that is parallel to axes 111 and 121, the second connector (150) extends in a direction that is transversal to the above-mentioned axes 111, 121 and 141 and links adjacent areas of proximal ends 122 and 142 of distal sections 120 and 140.

The second connector (150) is preferably joined to proximal ends 122 and 142 of sections 120 and 140 by means of, for example, laser welding.

This aspect of the invention can, naturally, be embodied by a range of variants in that the second connector (150) could form an integral part with distal sections 120 and 140 formed from a single part, while connector 130 would be joined by means of, for example, laser welding to the distal end of proximal section 110 and the proximal end of distal section 120.

In accordance with a particular embodiment, given as a non-exhaustive example, bifurcated endoprosthesis 100 for the coronary artery conforming with this invention has the following dimensions:

the total length of endoprosthesis 100 measured from proximal end 112 of proximal section 110 to distal end 123 of distal section 120 is of the order of 15 mm;

the diameter of sections 110, 120 and 140 is of the order of 1 mm prior to expansion;

the length of proximal section 110 is of the order of 7.5 mm prior to expansion;

the length of distal section 120 is of the order of 7 mm prior to expansion;

the length of distal section 140 is of the order of 9 mm prior to expansion;

the length of connector 130 is of the order of 0.5 to 1 mm; and the diameter of distal sections 120 and 140 in their expanded state is of the order of 3 mm while the diameter of proximal section 110 is of the order of 3.5 mm.

A description now follows of the structure of the instrument fitted with a double asymmetric balloon conforming with this invention which is shown in FIG. 8 et seqq.

Essentially, this instrument (200) comprises two balloons (210 and 230). The first balloon (210) is of a length consonant with its purpose of being positioned inside two approximately aligned sections (T1 and T2) of vessel V for treatment: main stem T1 and a branching vessel T2, situated one on either side of the bifurcation area respectively, or, again, of being positioned inside proximal section 110 and distal section 120 of endoprosthesis 100.

As regards the second balloon (230), this is consonant with its purpose of being positioned in the second blood vessel (T3) branching off from the bifurcation. Balloon 230 is preferably shorter than balloon 210. As shown in the accompanying figures, the two balloons 210 and 230 are preferably formed from generally cylindrical elongated tubular items centred upon axes 212 and 232 and having their ends (214 and 216; 234 and 236) more or less rounded.

The main balloon (210) preferably incorporates a recess in its side (218) suitable for housing proximal end 236 of the second balloon (230) as shown in FIG. 10.

Furthermore, proximal portion 219 of balloon 210 located upstream of recess 217 is preferably of greater diameter than distal portion 217 of the same balloon located downstream of recess 218.

Each of the balloons 210 and 230 is preferably fitted with a radio-opaque tracer (220 and 240). Tracers 220 and 240 are preferably located at the centres of their respective balloons 210 and 230. Tracers 220 and 240 may, for example, be carried by hollow internal tubes 221 and 241 housing metallic guides 222 and 242 having as their centres axes 212 and 232 and passing axially through balloons 210 and 230 respectively. Tracers 220 and 240 are preferably located halfway along balloons 210 and 230.

Balloons 210 and 230 are prolonged at their proximal ends 216 and 236 by, respectively, tubes 224 and 244, of narrow cross-section, designed to feed and, consequently, dilate balloons 210 and 230.

Tubes 224 and 244 preferably house guides 222 and 242. More specifically, each of the two tubes 224 and 244 preferably has two lumina: the first lumen houses a guide (222 and 242) and opens into the associated internal tube (221 and 241) and the second lumen, used for inflating the balloons, opens into the inside surface of the balloons (210 and 230).

The above-mentioned internal tubes 221 and 241 and first lumina are not connected with the internal surface of balloons 210 and 230.

Furthermore, internal tube 221 inside the first balloon (210) is preferably off-centre with respect to axis 212 in order to allow for the presence of recess 218 as is seen in FIG. 8.

Inflation tubes 224 and 244 are joined at a certain distance from balloons 210 and 230 and are preferably attached by their proximal ends to a stiffer but both flexible and hollow common component 250 with two internal lumina (253 and 254) linked with inflation tubes 224 and 244 respectively or, more specifically, the said above-mentioned second inflation lumina of these tubes. Component 250 is, moreover, itself fitted at its proximal end (252) with two connection systems with fluid sources linked with lumina 253 and 254 respectively, allowing balloons 210 and 230 to be expanded. These connection systems may, for example, be of the type known as "Luer-Lock". A variant on this is that the above-mentioned connection systems may be adapted to take a standard inflation syringe tip.

It is important that the above-mentioned connection systems communicating with, respectively, lumina 253 and 254 formed inside component 250 should allow the two balloons (210 and 230) to be expanded separately.

Balloons 210 and 230 are preferably covered prior to use with a removable sheath (260). Sheath 260 covers the full length of endoprosthesis 100, i.e. preferably a minimum of 15 to 20 mm. Sheath 260 is preferably linked at its proximal end to a wire (262) facilitating removal of sheath 260 by pulling the said wire 262. Wire 262 preferably passes through common tube 250.

Sheath 260 can, however, be omitted when the balloon system alone is used, i.e. without endoprosthesis 100.

The "Luer-Lock" connection systems shown in FIG. 12 are referred to as 252. Furthermore, reference n° 270 in FIG. 12 labels a schematic inflation system comprising a pressure gauge (272) adapted for linkage to one of the connection system (252) with a view to dilating one of balloons 210 and 230.

Reference n° 253 and n° 254 in FIG. 13 label the two feeder lumina linking connection systems 252 with tubes 224 and 244 respectively. In addition, reference n° 255 in FIG. 13 labels the lumen housing the wire (262) facilitating the removal of sheath 260.

In accordance with a particular embodiment that is, naturally, non-exhaustive, asymmetric double balloon 200 for coronary angioplasty conforming with this invention has the following dimensions:

- guide-wires 222 and 242 are 0.036 cm (0.014 inch) guide-wires;
- the longer balloon (210) is 20 to 25 mm in length, depending on the model;
- its proximal portion (219) is approximately 3.5 mm in diameter and approximately 6.5 mm in length after inflation;
- recess 218 is approximately 3.5 mm in length;
- distal portion 217 is approximately 10 mm in length and approximately 3 mm in diameter after inflation;
- the second balloon (230) is approximately 13 mm in length and approximately 3 mm in diameter after inflation;
- tubes 224 and 244 are joined approximately 10 mm from the proximal end (216) of balloon 210;
- the lengths of the two tubes 224 and 244 between the point at which they join and common component 250 may range from approximately 20 to 30 cm;
- the overall length, including balloons 210 and 230 and their feeder tubes is preferably approximately 135 mm;
- the length of common tube 250 ranges from approximately 110 to 115 mm; and
- the outer diameter of the device with balloons 210 and 230 completely deflated preferably does not exceed 2 mm, so that the whole unit including the two balloons 210 and 230 and feeder tubes 224 and 244 may pass through an 8 F guiding-catheter with an internal diameter of 2.6 mm. The case is the same in the version of the balloon device fitted with endoprosthesis 100 and sheath 260.

The portion of tubes 224 and 244 that is located downstream of guide-wire exits 223 and 243 is preferably made of plastic.

The portion of tubes 224 and 244, including common portion 250, that is located upstream of exits 223 and 243 may be made of plastic or metal.

This tube (224, 244 and 250) must be as hydrophilic as possible in order to be able to slide inside its carrier catheter or guiding catheter.

It should be noted that balloons 210 and 230 are mutually independent. They are indirectly linked only in the area of common tube 250.

Guide-wires 222 and 242 preferably emerge from tubes 224 and 244 on the nearer side of common section 250, as is seen in FIG. 11. Exit points 223 and 243 of guide-wires 222 and 242 are preferably at a slight distance from each other and are marked differently for identification.

A description now follows of the process for installing endoprosthesis 100 using asymmetric double balloon 200 in accordance with this invention.

Prior to use, the unit combining the two balloons (210 and 230) and bifurcated endoprosthesis 100 is protected by covering sheath 260. This unit fitted with sheath 260 is firstly maneuvered close to the bifurcation stenosis area. Its position is monitored using radio-opaque tracers 220 and 240.

Once the balloon (210 and 230)/endoprosthesis (100) unit has arrived at the bifurcation, above-mentioned sheath 260 can be withdrawn by pulling wire 262.

After protective sheath 260 has been withdrawn, guide-wires 222 and 242, which have been inserted into blood vessels T2 and T3 branching off from the coronary bifurcation, are manipulated. Balloons 210 and 230, located respectively inside proximal section 110 and distal section 120 in the case of balloon 210 and inside distal section 140 in the case of balloon 230, are still in a deflated state at this stage. Once it has been ascertained that sections 120 and 140 of the endoprosthesis have been correctly positioned at the bifurcation using radio-opaque tracers 220 and 240 contained in the balloons, the balloons can be inflated.

To this end, the first asymmetric balloon (210), i.e. the longer balloon which facilitates expansion of the main structure (110) of the endoprosthesis and of section 120, aligned with it, is preferably inflated first. Typically balloon 210 thus increases proximal portion 110 of the endoprosthesis to 3.5 mm and distal portion 120 to 3 mm.

This is followed by inflation of the shorter balloon (230), whose proximal end 236 fills recess 218 in balloon 210. Inflating balloon 230 thus dilates section 140 of the endoprosthesis. The proximal tapered shape of section 140 fits into the truncated form or form with its corner missing (115) of the main or proximal structure (110) of the endoprosthesis opposite and thus completely covers the ostial portion or bifurcation area of the coronary branching artery dilated and stented in the course of this procedure.

Once the bifurcated endoprosthesis has been deployed and installed, as shown in FIG. 7, balloons 210 and 230 can be deflated and withdrawn.

Balloons 210 and 230 can be deflated and withdrawn simultaneously or separately, as appropriate, after being detached from the unit.

It is advantageous for balloons 210 and 230 to be made from an elastic material manufactured from a plastic polymer.

This invention is not, of course, restricted to the particular embodiment described above but stems to any and all variants consistent with the idea embodied.

In particular, the invention is not limited to dilation of a bifurcation area in a coronary artery showing a lesion at the bifurcation using endoprosthesis 100 and employing dilation of balloons 210 and 230. The invention may also apply to other blood-vessel bifurcations, arteries or veins, such as, for example and non-limitatively, renal arteries, supra-aortic trunci, arteries leading from the aorta to the abdomen or to the low limbs, etc.

A particular variant of the invention is one in which balloon 210 may incorporate two portions (217 and 219), distal and proximal respectively, located on either side of recess 218 and having the same diameter.

During deployment, balloon 230 may be inflated before balloon 210.

Furthermore, installation and dilation of bifurcated endoprosthesis 100 may be envisaged using systems other than the double balloon structure illustrated in FIG. 8 et seqq., and, in a corollary manner, the double-balloon system (200) may be used as a double balloon for coronary bifurcation lesion angioplasty not involving use of an endoprosthesis.

According to a variant of the invention, the first balloon 210 is symmetric about its longitudinal axis 212. In other words the recess 218 is annular and symmetric of revolution about this axis 212.

What is claimed is:

1. An endoprosthesis for the treatment of blood-vessel bifurcation stenosis, comprising three tubular sections and two articulation connectors namely:

a proximal section;

a first distal section aligned at least approximately with the proximal section and intended for insertion into a first blood vessel branching off from the bifurcation, the first distal section being linked to the proximal section by a lateral first connector; and a second distal section located at the side of the first distal section and intended for insertion into a second blood vessel branching off from the bifurcation, both distal sections having their proximal ends linked by a second connector which allows relative pivoting of said distal sections about said second connector to accommodate the blood-vessel bifurcation, wherein the distal end of the proximal section is chamfered and the proximal end of the second distal section is tapered at the other side of the second connector and able to fit into the chamfered form of the proximal section.

2. An endoprosthesis according to claim 1 wherein the chamfer form is delimited by a flat surface.

3. An endoprosthesis according to claim 1 wherein the tapered section is delimited by a flat surface.

4. An endoprosthesis according to claim 1 wherein the chamfer form is delimited by a curved surface.

5. An endoprosthesis according to claim 1 wherein the tapered section is delimited by a curved surface.

6. An endoprosthesis according to claim 1 wherein the three tubular sections are of identical diameter prior to use.

7. An endoprosthesis according to claim 1 wherein the first connector has at its centre a plane of symmetry determined by the axes of the tubular sections and extends in a direction that is approximately parallel to these axes.

8. An endoprosthesis according to claim 1 wherein the first connector is formed from the same part as the proximal section and the first distal section.

9. An endoprosthesis according to claim 1 wherein the second connector has as its centre a plane of symmetry determined by the axes of the tubular sections and extends in a direction approximately perpendicular to these axes.

10. An endoprosthesis according to claim 1 wherein each of the sections is formed from a tubular component with a grid pattern of slits susceptible of expansion circumferentially.

11. An endoprosthesis for the treatment of blood-vessel bifurcation stenosis, comprising three tubular sections and two articulation connectors namely:

a proximal section;

a first distal section aligned at least approximately with the proximal section and intended for insertion into a first blood vessel branching off from the bifurcation, the distal section being linked to the proximal section by a lateral first connector; and a second distal section located at the side of the first distal section and intended for insertion into a second blood vessel branching off from the bifurcation, both distal sections having their proximal ends linked by a second connector which allows relative pivoting of said distal sections about said connector to accommodate the blood-vessel bifurcation, wherein the three tubular sections are of identical diameter prior to use and wherein the distal end of the proximal section is chamfered and the proximal end of the second distal section is tapered at the other side of the second connector and able to fit into the chamfered form of the proximal section.

12. An endoprosthesis according to claim 11, wherein the chamfer form is delimited by a flat surface.

13. An endoprosthesis according to claim 11, wherein the tapered section is delimited by a flat surface.

14. An endoprosthesis according to claim 11, wherein the chamfer form is delimited by a curved surface.

15. An endoprosthesis according to claim 11, wherein the tapered section is delimited by a curved surface.

16. An endoprosthesis according to claim 11, wherein the first connector has at its centre a plane of symmetry determined by the axes of the tubular sections and extends in a direction that is approximately parallel to these axes.

17. An endoprosthesis according to claim 11, wherein the first connector is formed from the same part as the proximal section and the first distal section.

18. An endoprosthesis according to claim 11, wherein the second connector has as its centre a plane of symmetry determined by the axes of the tubular sections and extends in a directions approximately perpendicular to these axes.

19. An endoprosthesis according to claim 11, wherein the second connector is attached to the two distal sections.

20. An endoprosthesis according to claim 11, wherein each of the sections (110, 120 and 140) is formed from a tubular component with a grid pattern of slits susceptible of expansion circumferentially.

21. An endoprosthesis for the treatment of blood-vessel bifurcation stenosis, comprising three tubular sections and two articulation connectors namely:

a proximal section;

a first distal section aligned at least approximately with the proximal section and intended for insertion into a first blood vessel branching off from the bifurcation, the distal section being linked to the proximal section by a lateral first connector; and a second distal section located at the side of the first distal section and intended for insertion into a second blood vessel branching off from the bifurcation, both distal sections having their proximal ends linked by a second connector which allows relative pivotment of said distal sections about said second connector to accommodate the blood-vessel bifurcation wherein the second connector has at its centre a plane of symmetry determined by the axes of the tubular sections and extends in a direction approximately perpendicular to these axes and wherein the distal end of the proximal section is chamfered and the proximal end of the second distal section is tapered at the other side of the second connector and able to fit into the chamfered form of the proximal section.

22. An endoprosthesis according to claim 21, wherein the chamfer form is delimited by a flat surface.

23. An endoprosthesis according to claim 21, wherein the tapered section is delimited by a flat surface.

24. An endoprosthesis according to claim 21, wherein the chamfer form is delimited by a curved surface.

25. An endoprosthesis according to claim 21, wherein the tapered section is delimited by a curved surface.

26. An endoprosthesis according to claim 21, wherein the three tubular sections are of identical diameter prior to use.

27. An endoprosthesis according to claim 21, wherein the first connector has as its centre a plane of symmetry determined by the axes of the tubular sections and extends in a direction that is approximately parallel to these axes.

28. An endoprosthesis according to claim 21, wherein the first connector is formed from the same part as the proximal section and the first distal section.

29. An endoprosthesis according to claim 21, wherein the second connector is attached to the two distal sections.

30. An endoprosthesis according to claim 21, wherein each of the sections is formed from a tubular component with a grid pattern of slits susceptible of expansion circumferentially.

* * * * *

UNITED STATES PATENT AND TRADEMARK OFFICE
CERTIFICATE OF CORRECTION

PATENT NO.    : 6,183,509 B1
DATED         : February 6, 2001
INVENTOR(S)   : Dibie It is certified that error appears in the above-identified patent and that said Letters Patent is hereby corrected as shown below:

<u>Title page,</u>
Item [76], Inventor, delete "37 avenue de Lowendale" and insert -- 37, Avenue de Lowendal --.

Signed and Sealed this

Fourth Day of February, 2003

JAMES E. ROGAN
*Director of the United States Patent and Trademark Office*